(12) United States Patent
Gysens et al.

(10) Patent No.: US 6,464,715 B1
(45) Date of Patent: Oct. 15, 2002

(54) INTENSIVE MULTIDIRECTIONAL PHOTOTHERAPY DEVICE

(75) Inventors: Lucien Gysens; Marie Yvonne Wauters, both of Charleroi (BE)

(73) Assignee: Medestime S.A., Charleroi (BE)

( * ) Notice: Subject to any disclaimer, the term of this patent is extended or adjusted under 35 U.S.C. 154(b) by 0 days.

(21) Appl. No.: 09/530,616

(22) PCT Filed: Oct. 30, 1998

(86) PCT No.: PCT/BE98/00164

§ 371 (c)(1),
(2), (4) Date: Aug. 15, 2000

(87) PCT Pub. No.: WO99/22813

PCT Pub. Date: May 14, 1999

(30) Foreign Application Priority Data

Oct. 30, 1997 (BE) .............................................. 9700872

(51) Int. Cl.[7] .............................................. A61N 5/006
(52) U.S. Cl. ............................. 607/91; 607/88; 607/93; 600/22; 237/3; 237/14; 200/61; D24/163
(58) Field of Search ............................... 607/88–94, 96, 607/100–103, 108, 112; 600/21, 22; 237/3, 14, 2 A; 435/809; D24/163; 200/61; 119/311, 319

(56) References Cited

U.S. PATENT DOCUMENTS

| | | | |
|---|---|---|---|
| 3,705,576 A | * 12/1972 | Roth .......................... 128/1 B |
| 3,877,437 A | * 4/1975 | Maitan et al. ............... 128/373 |
| 4,034,740 A | * 7/1977 | Atherton et al. ............ 128/1 B |
| 4,450,845 A | * 5/1984 | Engel ......................... 128/743 |
| 5,119,467 A | * 6/1992 | Barsky et al. ............... 392/439 |
| 5,316,542 A | * 5/1994 | Koch et al. ................... 600/22 |
| 5,336,248 A | * 8/1994 | Good et al. ................... 607/90 |
| 6,045,575 A | * 4/2000 | Rosen et al. ................. 607/88 |
| 6,290,713 B1 | * 9/2001 | Russell ........................ 607/88 |

FOREIGN PATENT DOCUMENTS

| | | |
|---|---|---|
| DE | 39 10 238 A1 | 3/1990 |
| FR | 2 193 628 A | 2/1974 |
| GB | 2 216 012 A | 10/1989 |

OTHER PUBLICATIONS

Sausville, J. et al. "Blue Lamp in Phototherapy of Hyperbilirubinemia" Journal of IES, pp. 112–116, Jan. 1972.*

* cited by examiner

*Primary Examiner*—Linda C. M. Dvorak
*Assistant Examiner*—Ahmed Farah
(74) *Attorney, Agent, or Firm*—Knobbe, Martens, Olson & Bear, LLP

(57) ABSTRACT

Disclosed is a phototherapy device for treating icterus in new-born patients, comprising a light box with at least one light source arranged in the box for illuminating the patient and a support for the patient to be placed upon which is at least partially transparent or tinted as to allow the light from the light box to expose the patient from below with respect to its direction of gravity, making it possible to expose areas having a high bilirubin concentration which tend to follow the direction of gravity.

19 Claims, 7 Drawing Sheets

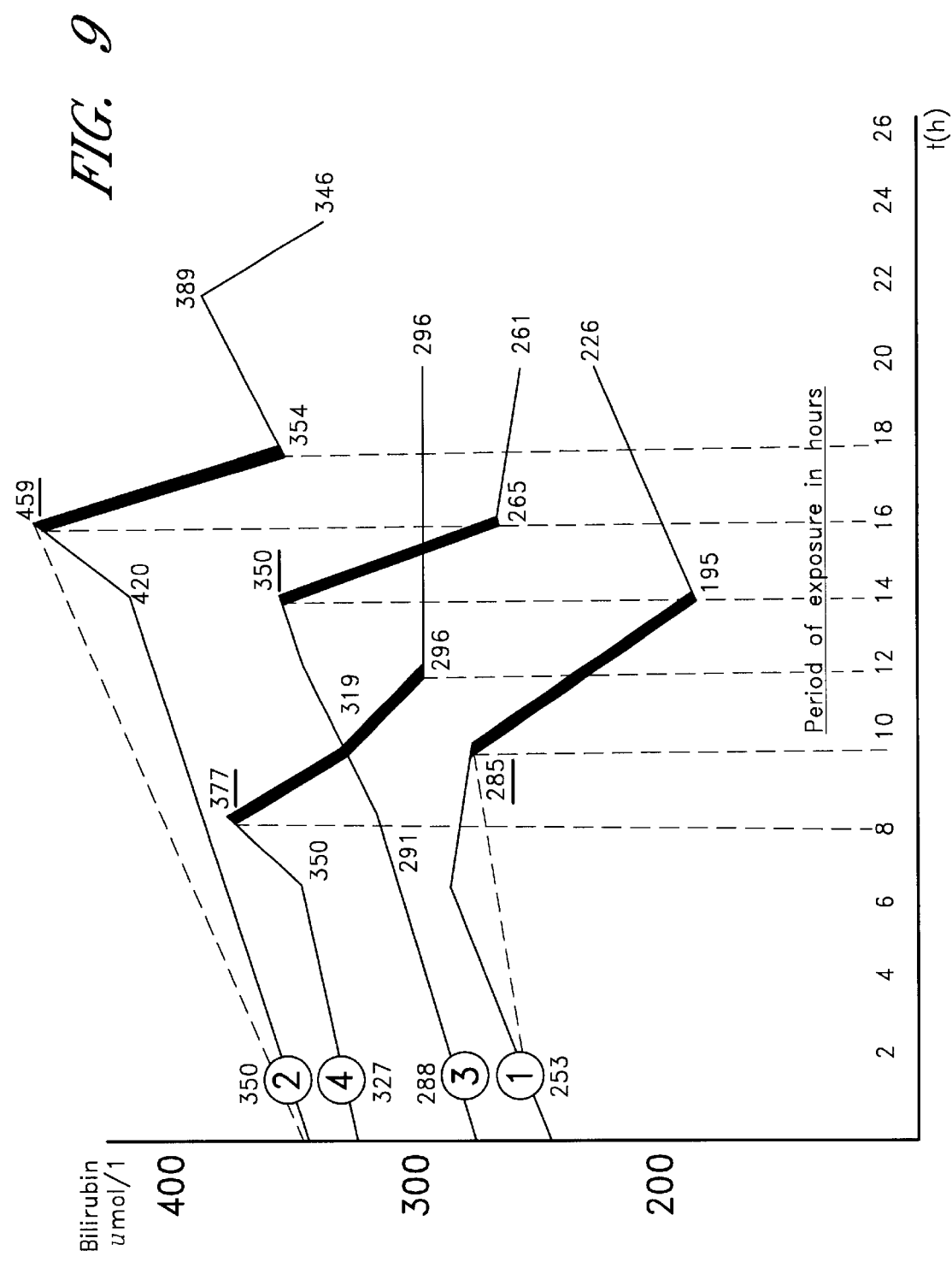

INTENSIVE MULTIDIRECTIONAL PHOTOTHERAPY DEVICE

This is the U.S. National Phase under 35 U.S.C. §371 of International Application PCT/BE98/00164, filed Oct. 30, 1998, which claims priority of Belgian application BE 9700872, filed Oct. 30, 1997.

SUBJECT OF THE INVENTION

The present invention relates to a so-called intensive multidirectional phototherapy device intended for treating a premature or full-term newborn suffering from severe icterus or liable to develop this.

TECHNOLOGICAL BACKGROUND AT THE BASIS OF THE INVENTION

The number of premature babies displaying serious icterus requiring exchange transfusion is on the increase. Since icterus can develop rapidly and exponentially, it is necessary to intervene very quickly if it is desired to prevent irreversible neurological damage. These premature babies must receive uninterrupted intensive care in incubators.

Until now, the treatment of icterus has consisted of an exchange transfusion making it possible to dissociate bilirubin which forms a poison before the transfusion of the newborn.

Given that most hyperbilirubinaemias are due to parental blood incompatibilities (incompatibilities with regard to rhesus factors, A, B, O, etc.), it is impossible to take blood from the parent in order to transfuse it to the newborn.

PRIOR ART

Neo-natal icterus has also been treated for many years in paediatric clinics by phototherapy of the skin of the newborns.

Document GB-A-2,216,012 describes an apparatus comprising an incubator made of a transparent material, provided in its upper part with a complex of fluorescent tubes placed parallel to one another beneath a reflecting surface so as to illuminate the newborn lying inside the incubator from above.

A support comprising such an incorporated reflecting surface is also described in Patent Application DE-A-3,910,238. This type of apparatus and of support requires the service personnel to turn the newborn frequently so as to irradiate his skin as uniformly as possible on all sides. This entails increasing the duration of the therapy and a certain amount of discomfort for the newborn, with the difficulty of obtaining truly uniform treatment over all parts of his skin.

Document FR-A-2,193,628 describes a particularly complex and bulky phototherapy apparatus comprising a compartment entirely made of a transparent material, including a bed on which the newborn is laid out and two groups of light sources placed respectively above and below the compartment. However, such an apparatus requires the use of large light tubes consuming a great deal of energy, given that the treated newborn is placed much too far from the light sources. However, the blue-light tubes normally used (Sansville et al., Journal of IES (January 1972)), which are effective in the treatment of icterus, are too long (possibly having a length of up to 520 mm for a 30 mm diameter) to create a device fitting in incubators. They require the use of ballasts and of on/off buttons to light them, these being liable to form a spark each time they are switched on. This is particularly dangerous during treatment in an incubator, which often requires oxygen concentrations exceeding 21% and possibly even up to 40 and 60%. As a result of the sparks generated, these apparatuses are excluded from being used for this purpose.

The desire of specialists is to have available a system which makes it possible to care for infants in serious distress having to undergo both intensive care, in an incubator or closed chamber, and effective intensive phototherapy that can be tailored according to the seriousness of the icterus they are developing, while still maintaining suitable monitoring of the treated newborn.

Aim of the Invention

The aim of the present invention is to provide a novel phototherapy apparatus or device which does not have the drawbacks of the devices of the prior art and which is of simple and modular design, so as to be able to be used for the safe treatment of a newborn that is liable to develop icterus or has icterus already, particularly in an incubator or closed chamber, so as to limit or avoid any traumatism in the newborn, particularly from exchange-transfusion operations.

Characteristic Elements of the Invention

The present invention relates to a so-called intensive phototherapy device making it possible to treat a newborn (either premature or full-term) suffering from serious icterus, in a maternity ward, in his mother's room and even in a closed environment such as an incubator or closed chamber, while limiting or avoiding exchange transfusion and guaranteeing optimum safety of the newborn being treated.

The phototherapy device of the invention is intended to comprise, advantageously fastened to the same frame, a light box which includes at least one light source (the said light source being designed in the light box to illuminate the said patient) and a support for the patient to be laid out on, the said support being at least partially (but essentially) transparent or tinted so as to let the light coming from the light box through.

In the phototherapy device of the invention, the support is placed above the light box so as to expose the patient (held on the support from below with respect to the direction of gravity), thus allowing better exposure of the areas having a high bilirubin concentration which are present in the patient's body and which tend to follow the direction of gravity.

According to the invention, the term "light box" should be understood to mean a hermetically sealed assembly capable of containing one or more light-emitting sources, such as tube lamps (or possibly other light sources connected to optical fibres), as well as all the components allowing these light sources to be modulated or turned off. The light box of the invention also incorporates various means ensuring that any excessive heating of fluids or gases which is caused by these light-emitting sources does not affect the patient to be treated and allows only the emission of light (which is preferably filtered, with no infrared and no ultraviolet) towards the newborn to be treated.

Furthermore, the light box of the invention includes external electrical connectors and air inlets/outlets making it possible to supply the various electrical, mechanical or electronic components of the device of the invention, particularly the light box, such as fans, air intake ducts and ducts for extracting air via suction cones, etc.

The thermal regulation system consists of an air extraction device comprising fans placed in the corners of the light box and allowing effective air flow towards the air suction and extraction cones.

The frame holding the light box and the support in an orientation allowing the patient to be exposed to the light is designed to allow the incorporation of the phototherapy device of the invention in an incubator or in a closed chamber.

For optimum safety, the light box is perfectly sealed and avoids any electrical or mechanical contact with components placed in the incubator or closed chamber. Such an arrangement prevents any spark or shock occurring which could have serious consequences for the patient.

According to the invention, the light sources are designed to generate light of greater than 3 mW per $cm^2$ of skin, preferably greater than 5 mW per $cm^2$ of skin, of the patient being treated. These light sources consist, for example, of lamps emitting blue or green light preferably having a spectrum of blue light mixed with green, these being tailored to any type of skin of a patient, including black or mulatto infants.

According to a preferred embodiment of the invention, use is made of light sources consisting of lamps whose spectral analysis reveals blue and green light in three bands (preferably of a wavelength ranging from 420 to 650 nm) and making it possible to deliver greater power of intense illumination than that in conventional tubes, with a broader available band and more rapid dissociation of bilirubin (particularly tube lamps of the $11/75$ D.Z.C type with a four-pin 2.G.7.4 cap and with a wavelength of 420 to 700 nm (such as those stipulated in the Commission Internationale d'Eclairage (code 1931) diagram)) (see FIG. 8).

These small tube lamps do not have an igniter and can be easily fitted into the light box of the invention. They allow them to be arranged in a geometry (see FIG. 2) which ensures effective emission of light onto the patient to be treated.

The phototherapy device of the invention may also include one or more domes which also incorporate light sources, the said domes being capable of exposing the patient (who is resting on the support) from above with respect to the direction of gravity of the said patient and are placed on the opposite side from the light box with respect to the support. Advantageously, the walls of the domes, of the light box and possibly of the frame comprise components which reflect the light emitted by the sources towards the patient to be treated, so as to ensure that all of the patient's skin is treated.

Furthermore, the light sources placed in the domes or in the light box are advantageously arranged in an alternating fashion along mutually opposed sides of the light box or of the dome, so as to allow crossed emission of light, conducive to the quality of the patient's illumination and allowing optimum air circulation in the light box or in the dome, thus avoiding any temperature change liable to affect the patient.

The device of the invention may also comprise one or more means for controlling the emission of the light depending on the distribution of the bilirubin in the body of the patient to be treated, and/or an additional light source or device level with the position of the patient's head, which is an area liable to have a higher bilirubin concentration.

This control means may, for example, be a thermostat which automatically stops or reduces the illumination or which triggers fans, making it possible to lower the temperature within the light box, within the dome or within the closed environment in which the newborn being treated lies. This thermostat system may be combined with a second means fastened directly to the new-born patient, such as a precision thermometer connected to an electronic thermostat fastened directly to the newborn (a cutaneous probe fastened to the patient's abdomen), which will control the temperature variations of the newborn. In the case of hyperthermia exceeding 39.5° C., a full-term newborn, and most particularly a premature newborn, may undergo convulsions. The device of the invention will make it possible to trigger various mechanisms for preventing such complications or will allow the medical personnel or nurses to be alerted (alarms able, where appropriate, to be connected to a central monitoring station).

Other systems for controlling the components involved in the device of the invention or the patient being treated may be designed by those skilled in the art according to improvements made to the apparatus for the treatment of newborns, or according to the disorders liable to affect the newborn.

According to the invention, the support of the device of the invention is made of a material which filters out or blocks the passage of ultraviolet and infrared radiation.

According to a preferred embodiment of the invention, the support includes a mattress, preferably a gel-type mattress, having a shape optimized for comfort and for ergonomics. Preferably, this gel-type mattress has one or more grooves, preferably in a criss-cross orientation, favouring the outflow of excrement from the new-born patient.

According to an alternative embodiment, the support includes or consists of a hammock, the meshes of which let through the light emitted by the light box or possibly reflected by the walls of the frame or of one or more domes.

According to another alternative embodiment, the support may include or consist of a sheet made of a material such as plexiglas which allows filtering (preferably of the "total screen" type) of the ultraviolet and infrared.

The other parts of the light box, of the domes or of the frame may be made of a conventional plastic such as polyurethane, which other parts are obtained by moulding or low-pressure injection moulding or are produced in a monobloc fashion. These various parts may be produced as a single piece or be adapted in a modular and ergonomic manner so as to favour the use and maintenance of the phototherapy device of the invention by the technical staff or nurses.

The light box may also be covered with a sheet forming a peripheral sealing skirt for the said box, the volume of which is designed so as to allow forced-air circulation in an incubator or chamber without impediment. In particular, the height of the walls of the end of the light box or of the frame incorporating in the light box 10 corresponds substantially to the height of the head of a patient lying down (a height of between 15 and 20 cm) so that the said wall slightly extends beyond the head of the patient lying down, thus forcing air to circulate above the patient without the latter being directly exposed thereto.

As mentioned above, the device may include one or more domes possibly integral with the frame of the phototherapy device of the invention or possibly fastened to an independent upright mounted on wheels. Advantageously, the domes fastened to an upright leave a space for the incorporation of other supply means or other means for treating the patient (a baxter, heating system, fans, etc.).

The height or the angle of the domes or the uprights supporting these domes may advantageously be adjusted, depending on the type of treatment to be given to the patient.

Another aspect of the present invention relates to a method of treatment and/or of prevention of icterus, characterized by a high bilirubin concentration in a premature or full-term newborn, which consists in treating the said newborn with sufficient emission of light by the phototherapy device of the invention so as to cause a drop in the bilirubin concentration in the patient being treated, as shown in FIG. 9.

Further features and characteristics of the invention will appear in the detailed description of the invention and the following examples with reference to the appended figures.

BRIEF DESCRIPTION OF THE DRAWINGS

FIG. 9 shows a summary of the results obtained by the device of the invention.

EXAMPLES

Example 1

Figure 1:
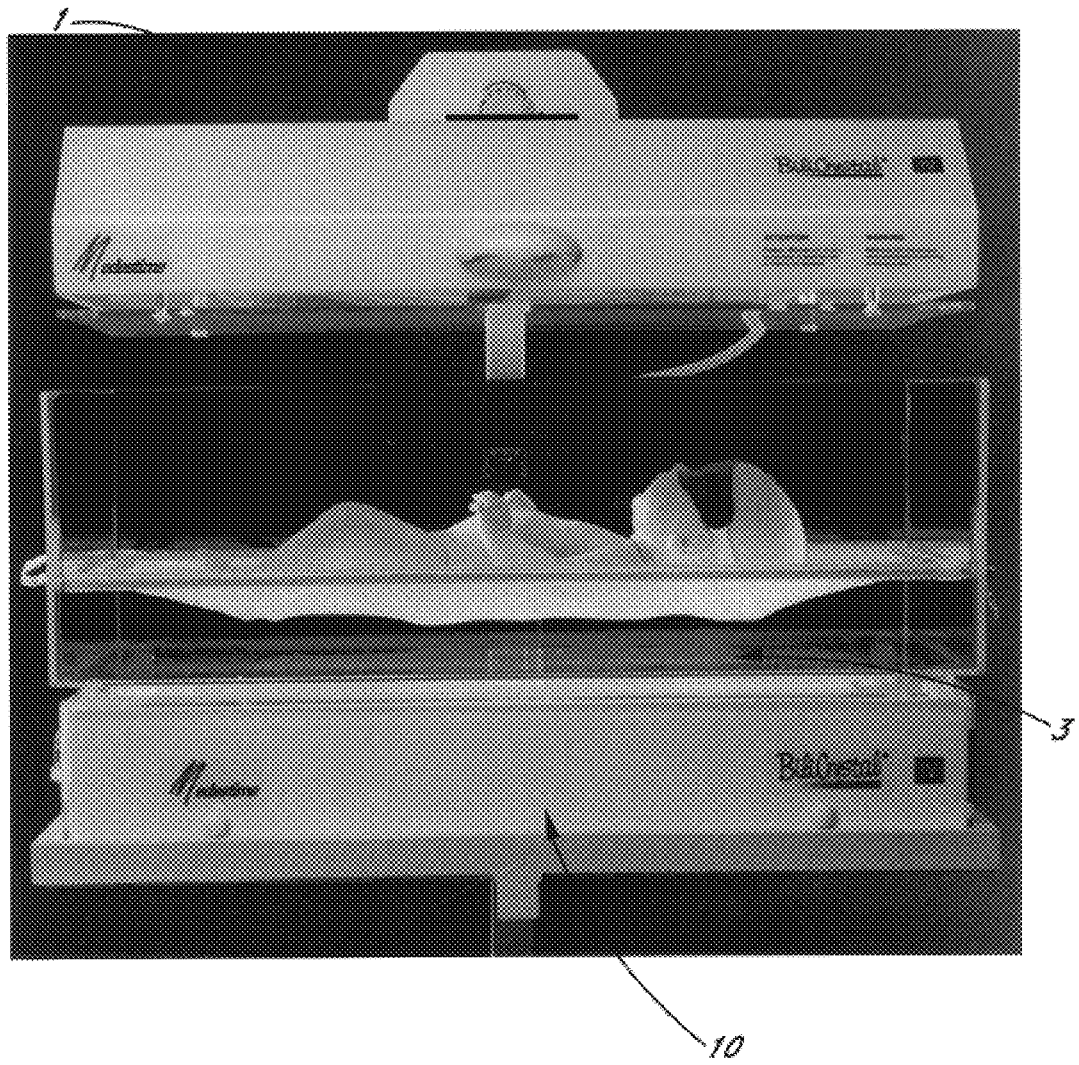
FIG. 1 represents a full view of the device of the invention.
Figure 2:
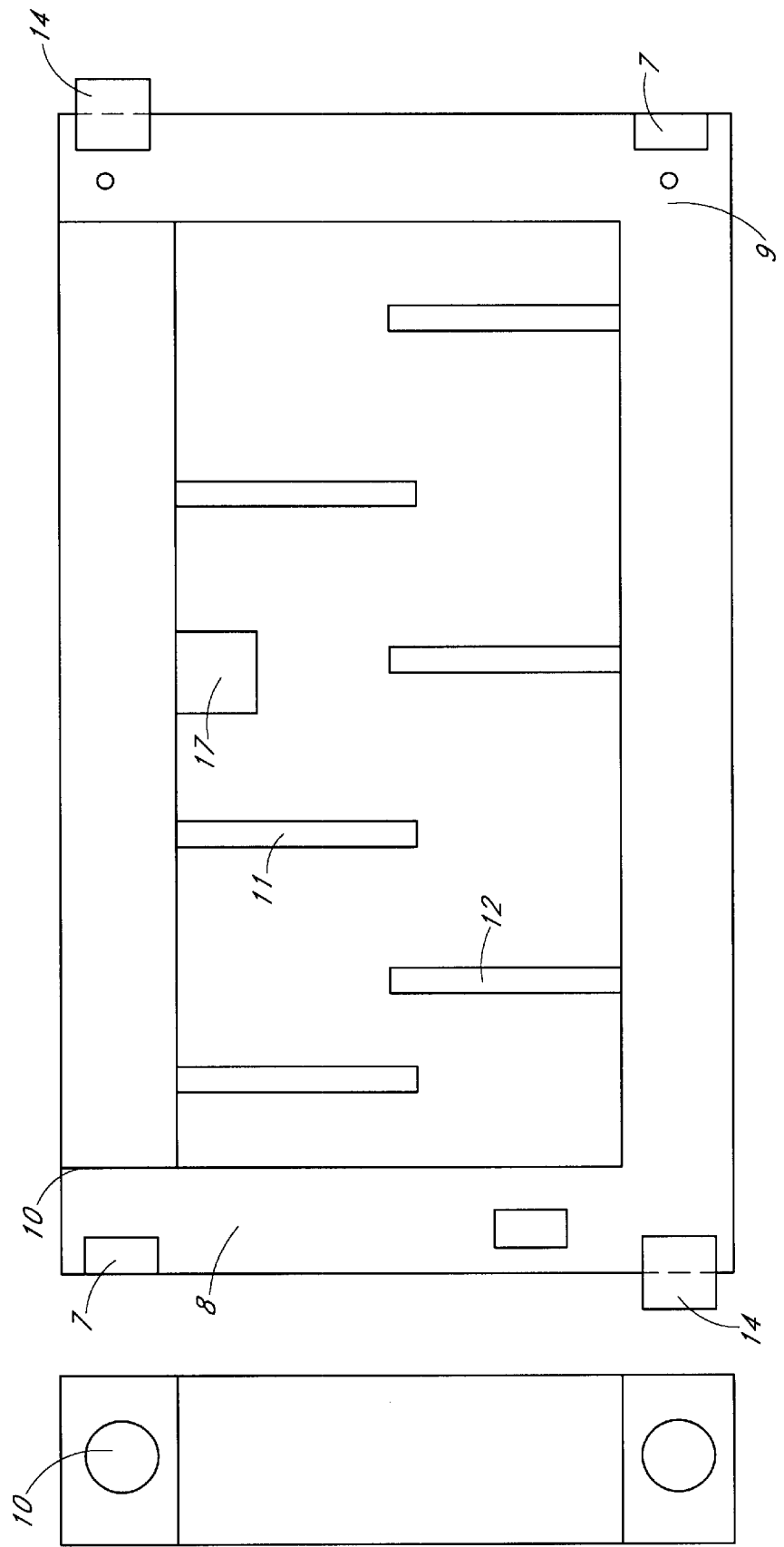
FIGS. 2 and 3 show schematic plan views of the particular arrangements of the light box of the device of the invention.
Figure 3:
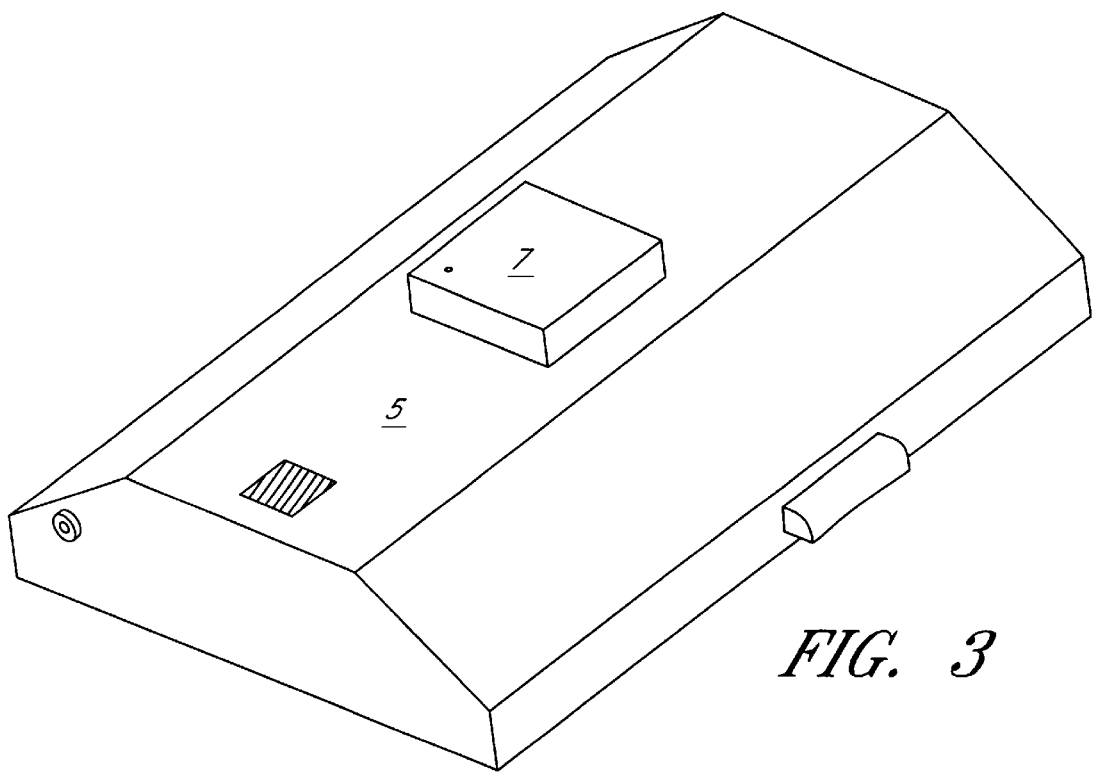
Figure 4:
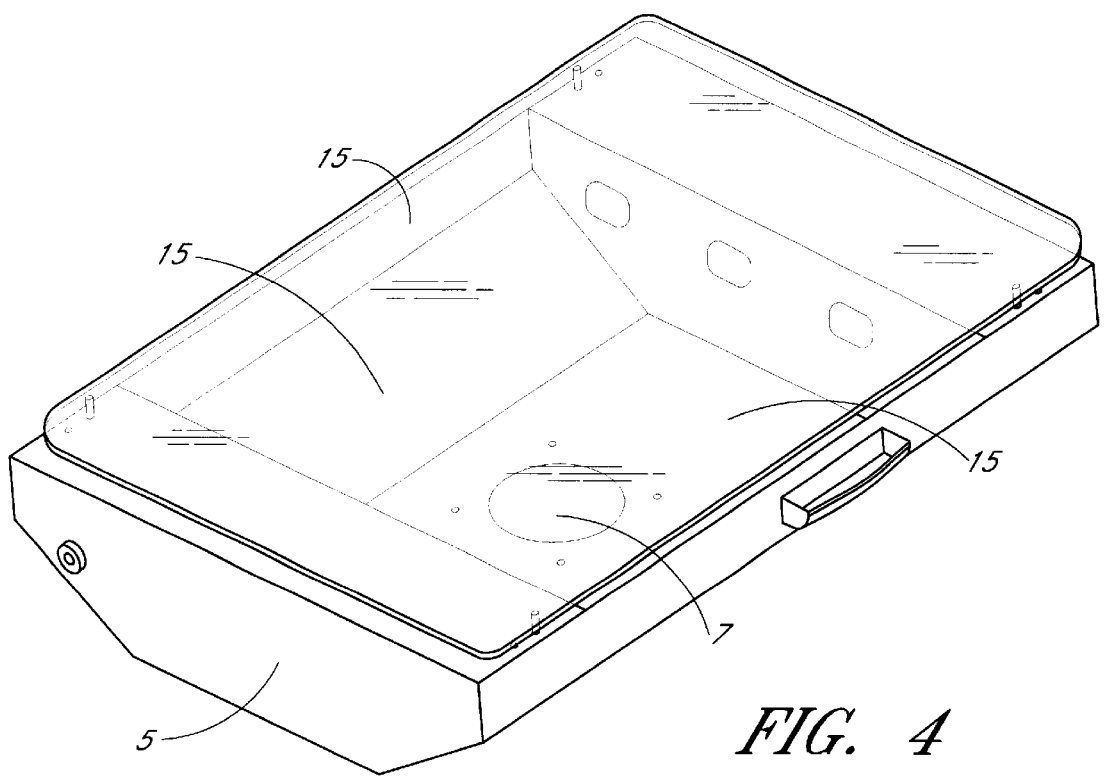
FIGS. 4 and 5 show perspective views of the light box of the invention.
Figure 5:
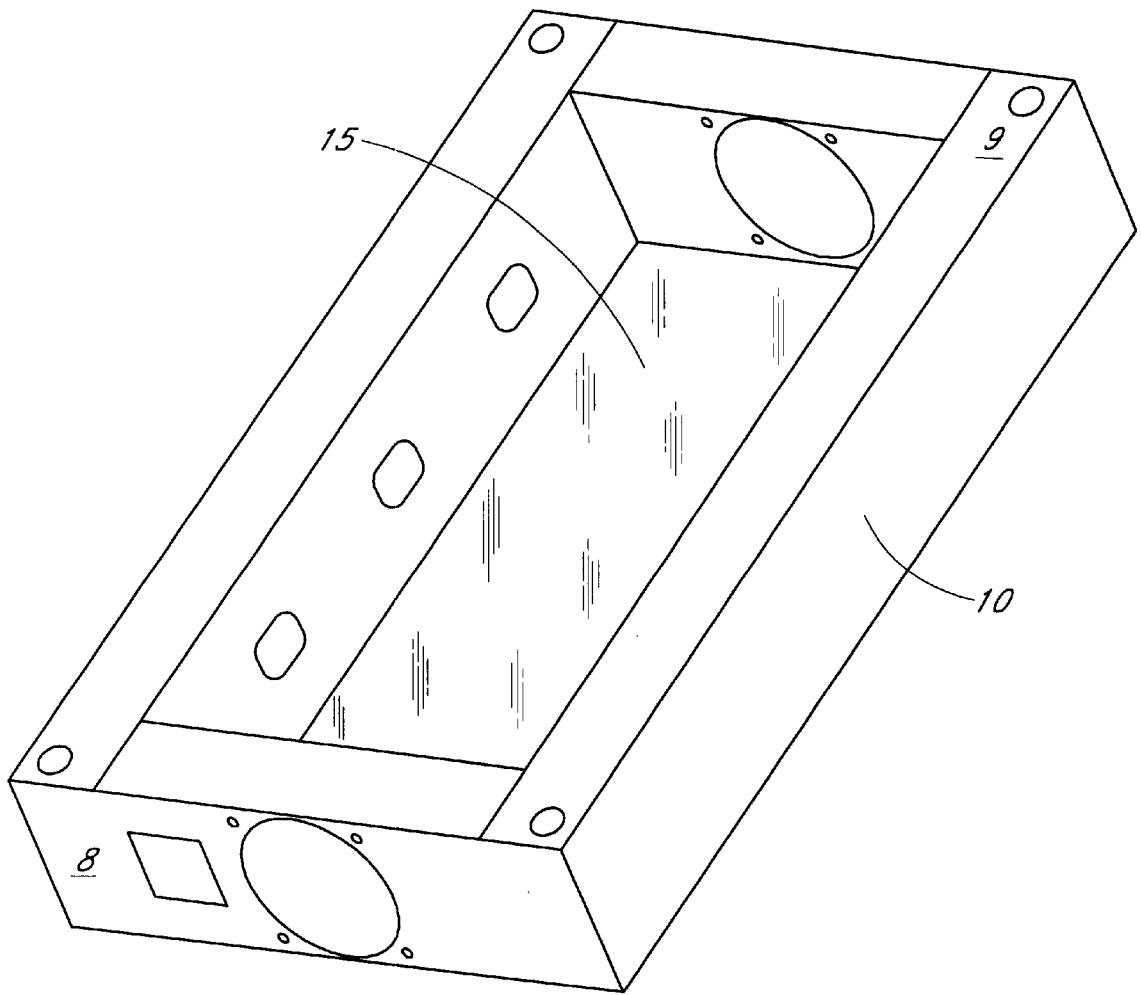

The phototherapy device 1 as shown in FIGS. 1 to 8 comprises a frame 2 supporting a light box 10 and a support 3 for the patient to be treated (which consists, in FIG. 1, of a hammock 6 suitable for the patient to be treated). Above the patient, the frame 2 also supports a single dome 5 illuminating the newborn from above.

Figure 7:
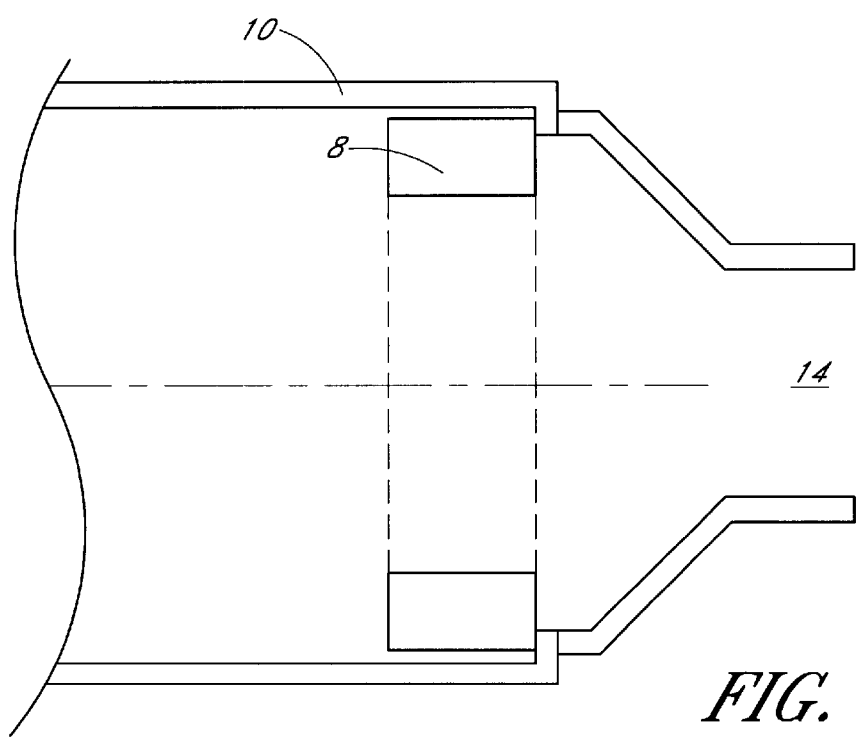
FIG. 7 shows the upright supporting the domes and the support of the device of the invention.

The light box 10 as shown in FIGS. 2 to 5 has a succession of lamps 11, 12 arranged along the mutually opposed sides 15, 16 of the light box 10. Incorporated into the corners 8 and 9 of the light box 10 are fans 7 allowing effective flow of air towards extraction ducts 14, optionally via extraction cones as shown in FIG. 7.

Advantageously, the light box 10 also includes a temperature-control device, triggering a thermostat 17 which causes the lamps 11, 12 to be turned on or off and causes the aforementioned fans 7 to be operated.

Figure 6:
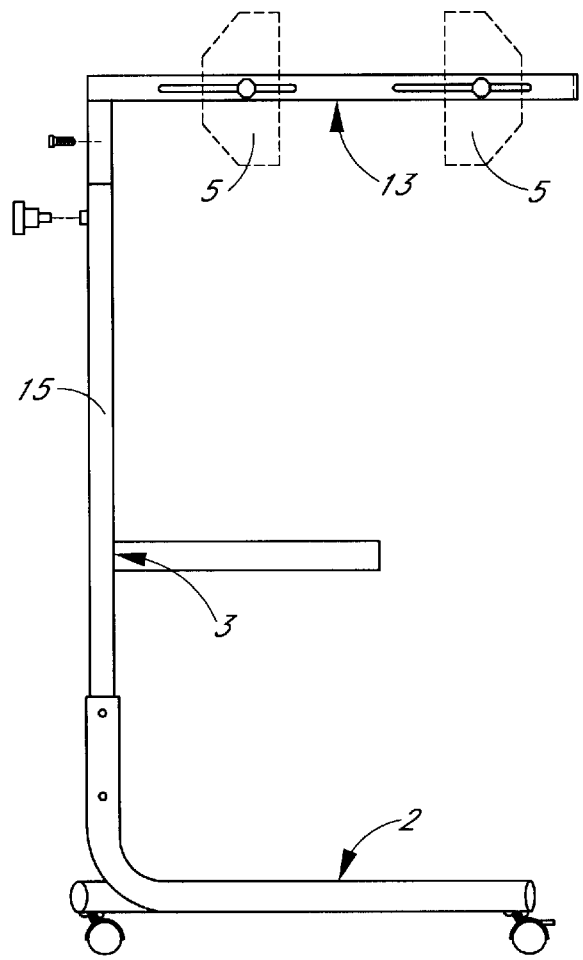
FIG. 6 shows a perspective view of the domes of the device of the invention.

As shown in FIG. 6, the device may include several domes 5 which can be adjusted by a knob 18 and leaves between the said domes 5 a space 13 into which may be incorporated a heating device, a Baxter, etc.

The domes 5 may be held by an upright 15 independent of the frame 2 supporting the light box 10 and the support 3 or they may be integral with the said frame 2.

The bottom or the side walls of the light box 10 or of the domes 5 may include one or more reflective elements 15 placed so as to ensure optimum illumination of the patient (preferably the entire surface of the patient's skin should be illuminated).

Figure 8:
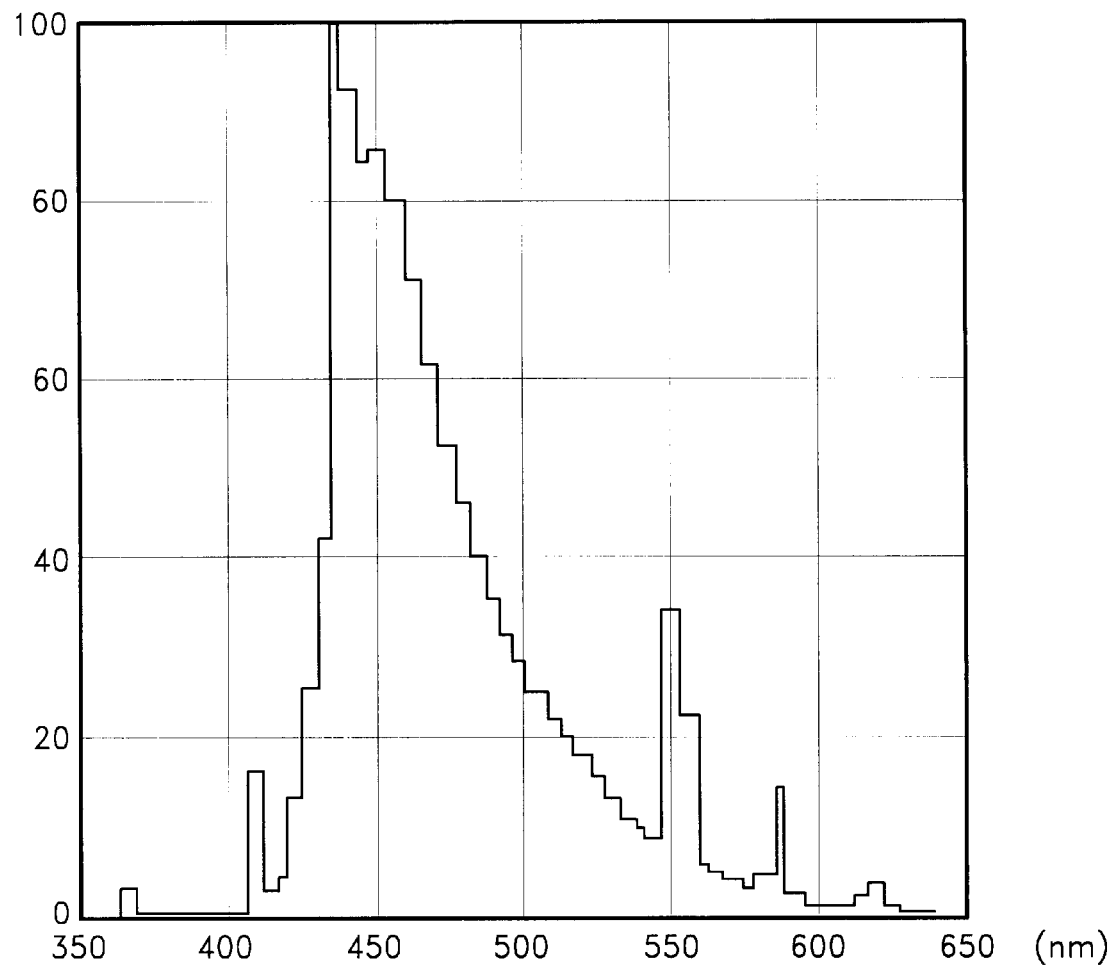
FIG. 8 shows the emission diagram for the light used in the device of the invention.

The light sources consist of tube lamps 11, 12, the light spectrum of which is shown in FIG. 8 (a spectrum of blue light mixed with green). However, other types of spectra tailored to the skin of a patient, such as a black infant or a mulatto infant, may be used with a greater amount of green light.

Example 2

The phototherapy device of the invention was used to treat various newborns suffering from serious icterus, allowing intense illumination of light, particularly of the blue component delivered by the tube lamps, having values of greater than 2 mW per $cm^2$, preferably values greater than 4 mW per $cm^2$, of skin. The newborns being treated were kept under supervision by the monitoring means of the invention and under medical supervision, which guarantee that the infant is exposed to the light correctly.

The device of the invention makes it possible to fulfil the conditions in circular BH No. 21 from the French Ministry of Social Affairs, Health and Life, since it meets the main parameters required, namely a suitable light source, a suitable distance from the source to the infant, a treatment of the entire cutaneous surface of the infant with the proviso that no retinal lesion shall affect the newborn being treated, suitable centring of the infant beneath the light source, and a high-performance modular apparatus which is easy to maintain.

FIG. 9 shows that 4 patients treated by the device of the invention exhibited, after a short period of exposure, a drop in their bilirubin concentration (bold black line). The patients were then treated according to conventional phototherapy. The short period of time during which the infants are treated by the phototherapy method of the invention is sufficient to allow a significant drop (of 23 to 30%) in bilirubin and to bring the patient out of the danger zone. Following this treatment, what is observed is either a steady bilirubin content or a new rise in this content following a switch to a conventional phototherapy, demonstrating the difference in effectiveness between these two types of phototherapy.

What is claimed is:

1. A phototheray device for the treatment of icterus in new-born patients, comprising a light box comprising at least one light source arranged in the box so as to illuminate said patient, and a support for the patient to be laid out on, wherein said support is at least partially transparent or tinted so as to let the light coming from the light box through, wherein said support is placed above the light box to expose the patient held on this support from below with respect to his direction of gravity, making it possible to expose the areas having a high bilirubin concentration which tend to follow the direction of gravity, wherein the intensity of the light is greater than 3 mW per $cm^2$ of patient's skin.

2. The device according to claim 1, wherein the intensity of the light is greater than 5 mW per $cm^2$ of patient's skin.

3. The device according to claim 1 wherein the support comprises a material which filters out or blocks the passage of ultraviolet and infrared radiation.

4. The device according to claim 1 wherein the support comprises a mattress.

5. The device according to claim 1, comprising a hammock, with meshes which let the light emitted by the light box through.

6. The device according to claim 1 further comprising an additional light sources wherein said additional light source is level with the head of the patient to be treated.

7. The device according to claim 1 wherein the support comprises a sheet of polymethyl methacrylate.

8. An incubator or closed chamber comprising the phototherapy device according to claim 1.

9. The device according to claim 1, wherein said at least one light source comprises lamps having a spectrum selected from the group consisting of blue light, green light, and a mixture of blue and green light.

10. The device according to claim 9, wherein said at least one light source comprises lamps with a maximum intensity in the blue spectrum and the green spectrum having three bands, wherein said bands are of a wavelength between 420 and 650 nm.

11. The device according to claim 9, wherein the lamps do not have an igniter.

12. The device according to claim 9, wherein said at least one light source is arranged in an alternating fashion along mutually opposed sides of the light box.

13. The device according to claim 1 further comprising an external frame made of polyurethane.

14. The device according to claim 13, wherein the external frame is tinted in a color compatible with the spectrum of the light emission.

15. The device according to claim 14, wherein the external frame is tinted in a color such as white or pink.

16. The device according to claim 1, wherein the light box comprises a fan and a thermostat which modulates the emission of light by the said at least one light source.

17. The device according to claim 16, wherein the light box comprises an air suction and extraction device placed at the ends of the light box.

18. The device according to claim 1 further comprising one or more domes placed on the opposite side from the light box with respect to the support wherein said domes comprise one or more sources emitting light towards the patient to be treated.

19. The device according to claim 18, wherein the internal walls of the light box or the internal walls of the domes reflect the light emitted by the sources.

* * * * *

UNITED STATES PATENT AND TRADEMARK OFFICE
CERTIFICATE OF CORRECTION

PATENT NO. : 6,464,715 B1
DATED : October 15, 2002
INVENTOR(S) : Lucien Gysens and Marie Yvonne Wauters It is certified that error appears in the above-identified patent and that said Letters Patent is hereby corrected as shown below:

Column 6,
Line 35, please replace "phototheray" with -- phototherapy --.
Line 58, please replace "sources" with -- source, --.

Column 8,
Line 13, please replace "or" with -- and/or --.

Signed and Sealed this

Twenty-second Day of July, 2003

JAMES E. ROGAN
*Director of the United States Patent and Trademark Office*